US007820849B2

(12) United States Patent
Sielcken et al.

(10) Patent No.: US 7,820,849 B2
(45) Date of Patent: Oct. 26, 2010

(54) PROCESS FOR THE CARBONYLATION OF CONJUGATED DIENES USING A PALLADIUM CATALYST SYSTEM

(75) Inventors: Otto Erik Sielcken, Sittard (NL); Imre Toth, Geleen (NL); Henricus Anna Christiaan Baur, Herten (NL)

(73) Assignee: DSM IP Assets B.V., Heerlen (NL)

( * ) Notice: Subject to any disclaimer, the term of this patent is extended or adjusted under 35 U.S.C. 154(b) by 525 days.

(21) Appl. No.: 10/565,773

(22) PCT Filed: Jun. 28, 2004

(86) PCT No.: PCT/EP2004/007059

§ 371 (c)(1),
(2), (4) Date: Aug. 17, 2006

(87) PCT Pub. No.: WO2005/014520

PCT Pub. Date: Feb. 17, 2005

(65) Prior Publication Data

US 2007/0155984 A1 Jul. 5, 2007

(30) Foreign Application Priority Data

Jul. 25, 2003 (EP) ................................. 03077340

(51) Int. Cl.
*C07C 67/36* (2006.01)
*C07C 51/00* (2006.01)

(52) U.S. Cl. ....................... 560/204; 560/207; 562/497; 562/522

(58) Field of Classification Search ................. 568/429, 568/387; 560/204, 207, 114; 562/522, 497
See application file for complete search history.

(56) References Cited

U.S. PATENT DOCUMENTS

| 5,304,674 | A | * | 4/1994 | Drent | ............................ 560/204 |
| 5,495,041 | A | * | 2/1996 | Sielcken et al. | ............. 560/207 |
| 6,737,542 | B1 | * | 5/2004 | Drent et al. | .................. 560/207 |
| 6,835,850 | B2 | * | 12/2004 | Drent et al. | .................. 560/207 |

FOREIGN PATENT DOCUMENTS

WO          WO 02/26690        *    4/2002

* cited by examiner

*Primary Examiner*—Rosalynd Keys
*Assistant Examiner*—Yate' K Cutliff
(74) *Attorney, Agent, or Firm*—Nixon & Vanderhye P.C.

(57) ABSTRACT

A process is provided, in particular a continuous process for the carbonylation of butadiene by reacting the butadiene with carbon monoxide and a hydroxyl group-containing compound in the presence of a palladium catalyst system in a reaction zone to form a reaction mixture, said catalyst system comprising (a) a source of palladium cations, (b) a mono-, bi- or multidentate phosphine ligand, containing at least one phosphorus atom which is directly bound to two or three aliphatic carbon atoms, as process ligand to produce a palladium-phosphine ligand complex catalyst, and (c) a source of anions, said process ligand (b) containing the moiety shown in formula (I),

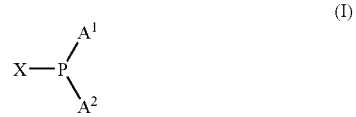

wherein $A^1$ and $A^2$ each represent an aliphatic carbon atom which can be connected to one or more aliphatic or aromatic carbon atoms or both $A^1$ and $A^2$ are part of an at least 5-membered ring including the phosphorus atom, and X represents an aliphatic or aromatic carbon atom which can be connected to one or more aliphatic or aromatic carbon atoms or X is part of an organic bridging group connecting another identically or differently substituted phosphorus atom, and said source of anions (c) containing a carboxylic acid and, optionally, halide ions, wherein said process ligand is fed continuously or periodically to the process as ligand make-up at a temperature 50° C. or lower.

18 Claims, 2 Drawing Sheets

PROCESS FOR THE CARBONYLATION OF CONJUGATED DIENES USING A PALLADIUM CATALYST SYSTEM

This application is the U.S. national phase of international application PCT/EP2004/007059 filed 28 Jun. 2004 which designated the U.S. and claims benefit of EP 03077340.2, dated 25 Jul. 2003, the entire content of which is hereby incorporated by reference.

FIELD OF INVENTION

The present invention relates to a process for the carbonylation of a conjugated diene by reacting the conjugated diene with carbon monoxide and a hydroxyl group-containing compound in the presence of a palladium catalyst system. In particular, the process of the present invention relates to the carbonylation of 1,3-butadiene to prepare alkylpentenoates and/or dialkyladipates.

BACKGROUND AND SUMMARY OF INVENTION

Such a process is known from WO-A-02/26690 which discloses the carbonylation of a conjugated diene by reacting said conjugated diene with carbon monoxide and a hydroxyl group-containing compound in the presence of a catalyst system based on (a) a source of palladium cations, (b) certain bidentate diphosphine ligands, and (c) a source of anions. The latter component includes carboxylic acids such as pivalic acid, and monoesters of dicarboxylic acids such as monomethyladipate. According to the description typical bidentate ligands include 9-phosphabicycloalkylalkanes, such as 1,2-bis (9-phosphabicyclononyl)propane, 2,3-bis(9-phosphabicyclononyl)butane, and 2,3-bis(9-phosphabiscyclononyl)pentane, and the like.

It is further stated in said WO-A-02/26690that the carbonylation process of conjugated dienes when carried out with such a specific choice of diphosphine ligand exhibits unexpected advantages with regard to the catalyst activity and, in addition, that the catalyst system remains stable over a prolonged period of time and can be reused several times without loss or substantial loss of catalyst activity. As described, the process is preferably carried out with a slight molar excess of ligand to palladium because this results in that the ligand degradation is decreased or even no ligand degradation occurs. Most preferably, the bidentate ligand/palladium molar ratio is higher than 1.05 and less than 1.2. When performing the process with a slight excess of ligand to palladium, it is preferred to monitor the concentration (and degradation) of the ligand and to add fresh ligand in order to remain in the preferred ranges of operation.

Despite the advantages and progress provided by the process and palladium catalyst system disclosed in the said WO-A-02/26690, the Applicant has found that the catalyst system and especially the ligand which is present in excess to Pd has only a moderate stability.

An object of the present invention is to provide an improved process in terms of stability of the catalyst system.

Without wishing to be bound to any particular theory, applicant has found that the bidentate diphosphine ligands which were applied in WO-A-0226690, such as the above-mentioned bis(9-phosphabicycloalkyl)alkanes but also other mono-, bi- and multidentate phosphine ligands containing at least one phosphorus atom which is directly bound to two or three aliphatic carbon atoms in general, hereinafter collectively referred to as the process ligand, tend to react with for example 2-pentenoic acid derivatives and/or with butadiene and/or polybutadienes in the presence of carboxylic acids under the usual carbonylation conditions, resulting in phosphonium salts. It is believed that at least a portion of the resulting phosphonium salts is not reversible to the starting materials and decomposes to three-valent phosphorus derivatives other than the process ligand. The decomposition products thus formed give also phosphonium salts and decompose even further.

It was also found that the equilibrium between the phosphonium salts and the free ligands is shifted strongly towards the phosphonium salts. Thus, the formation of phosphonium salts resulting from the use of bis(9-phosphabicycloalkyl)alkane or other mono-, bi- and multidentate phosphine ligands containing at least one phosphorus atom which is directly bound to two or three aliphatic carbon atoms, as process ligand seems to represent a degradation path for the ligand resulting in a complete consumption of the available free ligand at some time under carbonylation conditions.

It was also found that adding fresh process ligand under the carbonylation conditions usually applied results in the instantaneous formation of phosphonium salts. Thus, the freshly added ligand is not or only partly available for the regeneration of the catalyst from sub-stoichiometric ligand-Pd species.

It has surprisingly been found that the formation of the above-mentioned phosphonium salts of bis(9-phosphabicycloalkyl)alkanes or other mono-, bi- and multidentate phosphine ligands containing at least one phosphorus atom which is directly bound to two or three aliphatic carbon atoms is relatively slow at 50° C. and negligible at room temperature. It has also surprisingly been found that the regeneration of the Pd catalyst from sub-stoichiometric ligand-Pd species in the presence of an excess amount of the free (fresh) process ligand is very fast at a temperature less than or equal to 50° C.

DETAILED DESCRIPTION OF PREFERRED EXEMPLARY EMBODIMENTS

The present invention therefore provides a process for the carbonylation of a conjugated diene, in particular butadiene, by reacting the conjugated diene with carbon monoxide and a hydroxyl group-containing compound in the presence of a palladium catalyst system, said catalyst system comprising (a) a source of palladium cations, (b) a mono-, bi- or multidentate phosphine ligand, containing at least one phosphorus atom which is directly bound to two or three aliphatic carbon atoms, as process ligand to produce a palladium-phosphine ligand complex catalyst, and (c) a source of anions, said process ligand (b) containing the moiety shown in formula (I):

wherein $A^1$ and $A^2$ each represent an aliphatic carbon atom which can be connected to one or more aliphatic, including olefinic, or aromatic carbon atoms or both $A^1$ and $A^2$ are part of an at least 5-membered ring including the phosphorus atom, and X represents an aliphatic or aromatic carbon atom which can be connected to one or more aliphatic, including olefinic, or aromatic carbon atoms or X is part of an organic bridging group connecting another identically or differently substituted phosphorus atom, and said source of anions (c) containing a carboxylic acid and, optionally, halide ions, wherein said process ligand is fed continuously or periodically into the process as ligand make-up at a temperature of 50° C. or lower.

It has been found that with the process of the present invention the stability of the catalyst system is improved. It has in particular been found that with the process of the present invention the added process ligand make-up is less sensitive for degradation. An additional advantage of the process of the present invention is that regeneration of the catalyst system from sub-stoichiometric ligand-Pd species is more efficient.

Examples for the process ligand of the invention include monodentate phosphines where $A^1$ and $A^2$ each represent an aliphatic carbon atom of an alkyl, an alkenyl, an alkylene, an alkylaryl, an alkenylaryl, an alkylenearyl group which can have a linear, a branched, a cyclic, or a multicyclic arrangement. The fragments containing $A^1$ and $A^2$ can be the same or different including any combinations of the above-described groups. Suitable groups include, methyl, ethyl, propyl, iso-propyl, butyl, 2-butenyl, 2-methyl-allyl, iso-butyl, t-butyl, cyclopentyl, cyclohexyl, 2-cyclohexenyl, norbornyl, limonyl, benzyl, ethylenebenzene etc. X for the monodentate ligand represents an aliphatic carbon atom of an alkyl, an alkenyl, an alkylene, an alkylaryl, an alkenylaryl, an alkylenearyl group, which can have a linear, a branched, a cyclic, or a multicyclic arrangement or X represents a carbon atom of an aryl group. The alkyl, alkenyl, alkylene, alkylaryl, alkenylaryl, alkylenearyl or aryl group containing X can also be heterosubstituted with one or more substituents. Examples of such heterosubstituents include chloride, bromide, iodide and groups of the general formula —O—H, —O—$R^1$, —$COR^1$, —$COOR^1$, —COOH, S—H, —S—$R^1$, —$COSR^1$, —$NH_2$, —$NHR^1$, —$NR^1R^2$, —$CONH_2$, —$CONHR^1$, —$CONR^1R^2$ in which $R^1$ and $R^2$, independently, represent alkyl groups having from 1 to 4 carbon atoms like methyl, ethyl, propyl, isopropyl and n-butyl. Suitable X-containing groups include, methyl, ethyl, propyl, iso-propyl, butyl, 2-butenyl, 2-methyl-allyl, iso-butyl, t-butyl, 3-(carboxymethyl)-butylene, 3-methoxybutylene, cyclopentyl, cyclohexyl, 2-cyclohexenyl, norbornyl, limonyl, phenyl, ortho-methoxyphenyl, benzyl, ethylenebenzene.

Other examples for a monodentate process ligand is selected from phosphines, where both $A^1$ and $A^2$ are a part of an at least 5-membered ring including the phosphorus atom and X is as defined above. More preferably, both $A^1$ and $A^2$ are part of a non-substituted or substituted cyclic group, which contains 6 to 12 ring atoms including the phosphorus. The cyclic group can be a monocyclic group, such as for example a phosphacyclohexyl or phosphacyclooctyl group, or a multicyclic group. Preferably the cyclic group is a bicyclic group, such as for example a 7-phosphabicycloheptyl, a 8-phosphabicyclooctyl or a 9-phosphabicyclononyl group. Most advantageously both $A^1$ and $A^2$ are part of a substituted or non-substituted 9-phosphabicyclononyl group. The 9-phosphabicyclononyl group can have several isomeric structures. In the process of the present invention the [3,3,1] and [4,2,1] isomers are preferred.

The phosphabicyclononyl ring can be suitably substituted with one or more suitable organic groups containing carbon atoms and/or hetero-atoms. Suitable substituents include groups containing hetero-atoms such as halides, sulfur, phosphorus, oxygen and nitrogen. Examples of such groups include chloride, bromide, Iodide and groups of the general formula —O—H, —O—$R^1$, —$COR^1$, —COO—$R^1$, —COOH, —S—H, —S—$R^1$, —$COSR^1$, —$NH_2$, —$NHR^1$, —$NR^1R^2$, —$CONH_2$, —$CONHR^1$, —$CONR^1R^2$ in which $R^1$ and $R^2$, independently, represent alkyl groups having from 1 to 4 carbon atoms like methyl, ethyl, propyl, isopropyl and n-butyl.

If a phosphabicyclononyl ring is substituted, it is preferably substituted with one or more alkyl groups, preferably having from 1 to 10 carbon atoms, more preferably from 1 to 4 carbon atoms. Linear, branched or cyclic alkyl groups can be used. Suitable alkyl groups include, methyl, ethyl, propyl, iso-propyl, butyl and iso-butyl. More suitably methyl groups are used. When the phosphabicyclononyl ring is substituted, it is substituted most preferably with two methyl groups.

In a preferred embodiment of the process of the present invention, a bidentate ligand is used as process ligand. In this case, $A^1$ and $A^2$ are as defined above and X represents an aliphatic or aromatic carbon atom of an organic bridging group connecting another identically or differently substituted phosphorus atom. More preferably the connected other phosphorus atom contains two directly bound aliphatic carbon atoms, which are not part of the bridge and the substituents containing these aliphatic carbon atoms are selected from the same organic groups as described above for $A^1$ and $A^2$. One or both of these groups can also be an organic bridging group connecting a third phosphorus atom or a third and a fourth phosphorus atoms, respectively, giving a multidentate ligand. However, the use of bidentate ligands instead of multidentate ligands is more preferable for the invention.

Advantageously, the directly bound aliphatic carbon atoms on the connected other phosphorus atom of a bidentate ligand are also a part of an at least 5-membered, most preferably 6 to 12-membered ring including the other phosphorus atom. The cyclic group for this second ring can be a monocyclic group, such as for example a phosphacyclohexyl or phosphacyclooctyl group, or a multicyclic group. Preferably, the cyclic group for the second ring is a bicyclic group, such as for example a 7-phosphabicycloheptyl, a 8-phosphabicyclooctyl or a 9-phosphabicyclononyl group. Most advantageously, the cyclic group for the second ring is a substituted or non-substituted 9-phosphabicyclononyl group. If the second phosphabicyclononyl ring is substituted, it is substituted by a substituent, which is selected from the above-described suitable and preferable ring substituents for the first 9-phosphabicyclononyl group. The second 9-phosphabicyclononyl group can also have several isomeric structures. In the process of the present invention also the [3,3,1] and [4,2,1] isomers are preferred for the second ring.

The X-containing bridging group for a bidentate ligand can be selected from any organic bridging groups containing 1 to 6 carbon atoms, which can be interrupted by a hetero atom, such as nitrogen, sulfur, silicon or oxygen atom. The bridging group refers to the chain, which gives the shortest connection between the two phosphorus atoms. Suitable examples for such X-containing bridging groups include alkylene, alkenylene, arylene, 1-aryl-2-alkylene, 1-aryl-3-alkylene, aryl-1,2-dialkylene, aryl-1,3-dialkylene, which can be optionally substituted by one or more substituents containing carbon atoms and/or hetero atoms such as halides, sulfur, phosphorus, oxygen and nitrogen. Preferably the X-containing bridging group is an alkylene group. More preferably the X-containing bridging group is a substituted alkylene group with at least one substituent and more preferably with at least two substituents.

Preferably the X-containing bridging group is an ethylene or a 1,2-benzylidene group. More preferably, the X-containing group is an ethylene group with at least one substituent. Most advantageously the X-containing group is an ethylene group with two substituents.

Suitable substituents on the ethylene or other bridging groups include alkyl, alkenyl, and alkylene groups, which can have a linear, a branched, a cyclic, or a multicyclic arrangement, as well as aryl groups and heterosubstituents. Examples of such heterosubstituents, which can be bound to the bridging group directly or to the hydrocarbon bridge-substituent indirectly, include chloride, bromide, iodide and groups of the general formula —O—H, —O—R$^1$, —COR$^1$, —COOR$^1$, —COOH, —S—H, —S—R$^1$, —COSR$^1$, —NH$_2$, —NHR$^1$, —NR$^1$R$^2$, —CONH$_2$, —CONHR$^1$, —CONR$^1$R$^2$ in which R$^1$ and R$^2$, independently, represent alkyl groups having from 1 to 4 carbon atoms like methyl, ethyl, propyl, isopropyl and n-butyl. Alkylene, alkenylene substituents and/or heterosubstituents containing atoms, such as nitrogen, sulfur, silicon or oxygen on the ethylene or other bridging groups can also be connected to form a ring with the whole or a portion of the bridge.

Preferred substituents on an ethylene bridge group are alkyl and cyclic alkylidene groups, preferably having from 1 to 10 carbon atoms, more preferably from 1 to 6 carbon atoms. Linear, branched or cyclic alkyl groups can be used. Suitable alkyl groups include, methyl, ethyl, propyl, iso-propyl, butyl, iso-butyl, cyclopentyl and cyclohexyl groups. Suitable cyclic alkylidene groups involving the ethylene bridge include 1,2-cyclohexylidene and 1,2-cyclopentylidene groups. More suitably one or two methyl groups are used as substitutents on an ethylene bridge.

The most preferable process ligands to be used in the process of the present invention include 2,3-bis(9-phosphabicyclononyl) butane, 1,2-bis(9-phosphabicyclononyl)ethane, 1,2-bis(9-phosphabicyclononyl)propane, 1,2-bis(carboxymethyl)-1,2-bis(9-phosphabicyclononyl)ethane, 1,2-bis(hydroxymethylene)-1,2-bis(9-phosphabicyclononyl)ethane, 1,2-bis(methoxymethylene)-1,2-bis(9-phosphabicyclononyl) ethane 1,2-bis(9-phosphabicyclononyl)cyclohexane, 1,2-bis(9-phosphabicyclononyl)benzene, 1,2-bis(9-phosphabicyclononyl)cyclopentane, 3,4 bis(9-phosphabicyclononyl)hexane, 2-bis(dicyclohexylphosphino)-3-(9-phosphabicyclononyl) butane, 1,2-dicyclohexyl-1,2-bis(9-phosphabicyclononyl) ethane and 1-cyclohexy-1,2-bis(9-phosphabicyclononyl) ethane, and the like.

These ligands can be prepared as for example described in WO-A-02090368 and M.D. Fryzuk et al., *J.Am. Chem. Soc.*, 1977 (Vol.99), p. 6262-6267), or in a way analogous to the preparation of similar compounds which is known in the art. Suitable sources for palladium cations of component (a) include its salts, such as for example the salts of palladium with hydrogen iodide, hydrogen chloride, sulfuric acid or sulfonic acids and palladium complexes, e.g. with carbon monoxide or acetylacetonate. Preferably, a salt of palladium and a carboxylic acid is used, suitably a carboxylic acid with up to 12 carbon atoms, such as salts of acetic acid, propionic acid and butanoic acid, or salts of substituted carboxylic acids such as trichloroacetic acid and trifluoroacetic acid. A very suitable source is palladium(II) acetate.

The source of anions of component (c) is a carboxylic acid or a mixture of carboxylic acids. The pKa value of the carboxylic acid is preferably higher than 1 and more preferably the pKa is in the range from 1 to 6 (measured in an aqueous solution at a temperature of 25° C.). Exemplary carboxylic acids are benzoic acid, 2,4,6-trimethylbenzoic acid, acetic acid, valeric acid, 3-pentenoic acid, butanoic acid, or nonanoic acid. Also carboxylic acids corresponding with the diester (by-)products can be advantageously used in the process of the invention. The use of these acids is advantageous because they are readily obtainable by hydrolysis of these diester (by-)products. Examples of these acids are dicarboxylic acids like for example adipic acid, methylglutaric acid and ethylsuccinic acid; monoesters of dicarboxylic acids like for example monoalkyladipate, monoalkylmethylglutarate, monoalkylethylsuccinate and monoalkyl-2-propylmalonate, in particular monomethyladipate.

In another preferred embodiment the source of anions is a tertiary carboxylic acid, i.e. an acid with the formula (II):

$$R^3-C(R^5)-C(O)-OH \atop R^4 \qquad (II)$$

wherein R$^3$, R$^4$ and R$^5$ independently represent alkyl or aryl groups. Suitably the tertiary carboxylic acid used contains a total of from 5 to 20 carbon atoms, more preferably from 5 to 15 and most preferably from 8 to 10 carbon atoms.

Advantageously R$^3$, R$^4$ and R$^5$ are alkyl groups, preferably having from 1 to 16 carbon atoms, more preferably from 1 to 10 carbon atoms. Linear, branched or cyclic alkyl groups can be used. The alkyl groups may be substituted with aryl groups such as for example a phenyl group. Examples of suitable alkyl groups include methyl, ethyl, n-propyl, iso-propyl, n-butyl, iso-propyl, tert.-butyl and n-pentyl. Preferably at least one, and more preferably two, of R$^3$, R$^4$ and R$^5$ are, independently, a methyl or ethyl group.

Suitable tertiary carboxylic acids include 2,2-dimethylpropanoic acid (pivalic acid), 2,2-dimethyl butanoic-acid, 2-methyl-2-ethyl-butanoic acid, 2,2-dimethyl-pentanoic acid, 2-methyl-2-ethyl-pentanoic acid, isomers of tertiary C-9 acid (i.e. tertiary acids containing a total of 9 carbon atoms), isomers of tertiary C-10 acid, and isomers of tertiary C-11 acid. isomers of tertiary C-9 acid, isomers of tertiary C-10 acid, and mixtures thereof are preferred.

In the process of the invention one or more (a mixture) of the above-described carboxylic adds can be used as anion source.

Furthermore the presence of a substoichiometric amount of halide anions is preferred, based on the amount of palladium cations. The presence of a substoichiometric amount of halide anions has a favourable effect in that the carbonylation reaction proceeds at high rate, even at moderate temperatures. By "substoichiometric" is understood that less halide anions are present than required to neutralize the palladium cations, i.e. that the molar ratio of dissociated halide anions versus palladium cations is less than 2:1.

Preferably the source of halide anions is a source of chloride, bromide or iodide anions, and more preferably a source of iodide anions is used. Suitable sources of the halide anion include hydrogen halides, e.g. HCl, HBr and HI; quaternary ammonium or phosphonium halides, e.g., tetraethylammonium iodide, triphenylmethylphosphonium iodide, triphenylphosphonium bromide etc.; and metal halides e.g., NaCl, Na Br, NaI, MgBr$_2$, MgI$_2$, ZnCl$_2$, ZnI$_2$, LiI, LiBr, RbCl, CsCl, CsI, and CuCl, in particular alkali or earth alkaline metal halides. A preferred source of halide anion is hydrogen iodide.

In a special preferred embodiment hydrogen iodide is used as a source of anions in combination with a tertiary carboxylic acid such as pivalic acid, or with monomethyladipate, or with another monomethylester of a C6-dibasic acid, or with a mixture of these acids.

In the process of the present invention, an effective amount of process ligand is fed continuously or periodically to the process as ligand make-up at a temperature of 50° C. or lower, preferably at 40° C. or lower, more preferably at 30° C. or lower and even more preferably at room temperature. Preferably, the process is performed as a continuous process. The aforementioned advantage of improved stability and more efficient regeneration are further enhanced if the process of the present invention is carried out as a continuous process. In general, continuous carbonylation processes are well known in the art. Preferably, the following steps are performed in a continuous process for the carbonylation of a conjugated diene according to the process of the present invention:

(a) carbonylating the conjugated diene with carbon monoxide and a hydroxyl-group containing compound in the reaction zone in a liquid homogeneous reaction mixture comprising a solvent and the catalyst system;
(b) maintaining reaction temperature and pressure conditions favorable to the carbonylation of carbonylation of the conjugated diene;
(c) continuously supplying make-up quantities of the conjugated diene, carbon monoxide and the hydroxyl-group containing compound in to the reactor in which the carbonylation takes place;
(d) continuously withdrawing part of the reaction mixture from the reaction zone;
(e) separating from the withdrawn reaction mixture unreacted carbon monoxide, unreacted conjugated diene, unreacted hydroxyl-group containing compound and returning these reactants to step (a) and isolating alkylpentenoates and/or dialkyladipates and
(f) returning the remaining mixture of step (e) to step (a). Preferably a part of the remaining mixture of step (e) is separated from the mixture and led to a purge in order to prevent build up of high boiling by-products in the circulating reaction mixture Step (a) can be performed in several ways; for example, in a continuously stirred tank reactor or a bubble column in which the product is simultaneously stripped from the liquid phase.

Separating the carbon monoxide, conjugated diene, hydroxyl-group containing compound and the alkylpentenoates and/or dialkyladipates from the reaction mixture in step (e) can be performed in various ways. Generally the carbon monoxide is separated first from the reaction mixture, for example, in a simple gas-liquid separation unit. The conjugated diene, hydroxyl-group containing compound and the alkylpentenoates and/or dialkyladipates can be separated from the reaction mixture in one step followed by isolating alkylpentenoate and/or dialkyladipates from the conjugated diene and the hydroxyl-group containing compound. Preferably the conjugated diene and the hydroxyl-group containing compound are separated from the reaction mixture in a separate step followed by the isolation of alkylpentenoates and/or dialkyladipates from the remaining reaction mixture. Separation of the various compounds can be performed in various ways, for example by simple flash operation or by distillation.

The ratio of the remaining mixture of step (e) which is returned to step (a) and the part which is purged will depend on the amount of contamination (for example high boiling by-products) formed in the process and the acceptable level of contamination in the circulating process stream. The part which is sent to the purge will contain apart from the abovementioned contaminations also valuable palladium, the process ligand and carboxylic acid (source of anions). Preferably, palladium, the process ligand and carboxylic acid(s) are isolated from this mixture in order to advantageously reuse these compounds in the carbonylation step (step (a)) according to the invention. Examples of possible processes to separate these valuable compounds include distillation, crystallization and extraction. Preferably, extraction is used in order to separate these components.

In a preferred embodiment of the present invention, the ligand make-up is added to a reaction mixture containing at least a portion of the catalyst system, usually to a portion of the recycled catalyst solution before feeding the recycled catalyst solution to the reactor, at the temperature as defined above. Thus, in one aspect of the present invention a stream possibly containing sub-stoichiometric ligand-Pd species is contacted with an effective amount of fresh process ligand at 50° C. or below for efficient regeneration. In other words, the ligand/Pd ratio can be increased to 1:1 or above by contacting a stream of sub-stoichiometric ligand/Pd species with fresh process ligand at 50° C. or below, without substantial degeneration and/or formation of undesired by-products as described above. The ligand make-up can be added both continuously and periodically.

In the process of the present invention, it is essential that said portion of the reaction mixture, into which the ligand make-up is fed, has a temperature of 50° C. or below. Usually, prior to feeding the ligand make-up to said reaction mixture, the reaction mixture is cooled to a temperature of 50° C. or below.

As used herein, the term reaction mixture is meant a mixture containing an amount of the palladium-process ligand complex catalyst. The reaction mixture encompasses, but is not limited to, (a) the reaction medium obtained in the reaction zone, (b) the reaction medium stream on its way to the reaction product/catalyst separation zone, (c) the reaction medium in the reaction product/catalyst separation zone, (d) the catalyst mixture obtained in the reaction product/catalyst separation zone, (e) the recycle stream between the reaction product/catalyst separation zone and the reaction zone, (f) the mixture containing catalyst obtained in the high boiler purge/catalyst separation zone and (g) the mixture containing catalyst obtained in the dead ligand/catalyst separation zone (see FIG. 1). As used herein, with an effective amount of process ligand is meant said amount of process ligand which is sufficient to obtain a ligand to palladium molar ratio of at least 1. As used herein, with ligand make-up is meant said amount of process ligand which is fed periodically or continuously to the process in order to remain in the preferred range of ligand to palladium molar ratio.

In one embodiment of the invention, the process of the present invention further comprises separating reaction product from a reaction mixture containing the reaction product and the catalyst system to obtain a catalyst mixture containing at least a portion of said catalyst system and recycling at least a portion of said catalyst mixture to the reaction zone and the ligand make-up is added to said catalyst mixture prior to feeding said catalyst mixture to the reaction zone. In a further embodiment, the process of the invention further comprises separating high boiling compounds and/or dead ligand from said catalyst mixture and recycling the mixture containing catalyst obtained in the high boiler purge/catalyst separation zone and or obtained in the dead ligand/catalyst separation zone to the reaction zone and the ligand make-up is added to the mixture containing the catalyst prior to feeding said mixture to the reaction zone. In a further embodiment of the invention, said mixture containing catalyst is united with the catalyst mixture described above prior to feeding said catalyst mixture to the reaction zone resulting in a united catalyst mixture and ligand make-up is added to said united catalyst mixture.

In a preferred embodiment of the process, the concentration and degradation rate of the process ligand is monitored during the course of the carbonylation process and the ligand make-up is added to the process in an amount equivalent to the amount of the consumption of the process ligand.

In another aspect of the present invention it was found, that in contrast to the above-defined phosphine derivatives which are the preferred palladium process ligands in the carbonylation reaction, arylphosphines such as triarylphospines, for example triphenylphosphine, and diarylphosphines and derivatives thereof, such as bis(diphenylphosphino)alkanes, give reversible phosphonium salt formation under carbonylation conditions. In other words, such phosphines are in equilibrium with their phosphonium salts under carbonylation conditions. In addition, it was found that triarylphosphines generally coordinate weaker to Pd than bisdiarylphosphines which in turn coordinate weaker than the most of the above-described preferable process ligands. As a typical example of this finding it appeared that when an excess amount of a bis(9-phosphabicyclononyl)ethane derivative is used with Pd in the presence of an excess amount of triphenylphosphine or a bis(diphenylphosphino)alkane, only Pd-bis(9-phosphabicyclononyl)ethane derivatives are formed.

Therefore, the present invention further provides a process for the carbonylation of conjugated dienes, in particular butadiene, which comprises reacting the conjugated diene with carbon monoxide and a hydroxyl group-containing compound in the presence of a palladium catalyst system including a process ligand, as defined above, wherein a second phosphine ligand different from said process ligand is fed continuously or periodically into the process, wherein said second phosphine ligand is chosen such that its phosphonium salt is reversible under carbonylation conditions. More preferably, the second phosphine ligand is chosen such that the second phosphine ligand coordinates less strong to palladium than the process ligand. Thus, the second phosphine ligand preferably has less coordination strength in its complexes with palladium than said process ligand in palladium-process ligand complexes. Suitable examples of such second phosphine ligands are phosphine ligands containing at least one phosphorus atom which is connected to two aryl groups.

By less coordination strength is understood that a ligand of less coordination strength will not liberate a stronger coordinating ligand from its palladium complex. On the other hand by adding a stronger coordinating ligand to a palladium complex of a ligand of less coordination strength, the stronger coordinating ligand will replace the ligand of less coordination strength in the palladium complex. Anyone skilled in the art can judge whether a ligand has less coordination strength in a palladium complex than another ligand by carrying out the above-described substitution tests followed by an appropriate analysis, for example by $^{31}P$ NMR spectroscopy.

In a preferred embodiment of the invention, the second ligand is a compound selected from the group consisting of triaryl phosphines and bis(diarylphosphino)alkanes. Suitable compounds include, for example, triphenyl phosphine, a substituted triphenylphosphine, a trinaphthylphosphine, a substituted trinaphthylphosphine, or a bis(diphenylphosphino)alkane preferably having 2-8 carbons between the phosphorus atoms, straight or branched. When using the above mentioned most preferred process ligands, triphenyl phosphine and bis(diphenylphosphino)butane are preferred as second ligand.

The second ligand can be introduced into process at a different location and temperature as the first ligand. For example, the second ligand can be added directly into the reactor under the usually applied carbonylation conditions. The second ligand can also be added to a portion of the recycled catalyst solution before feeding the recycled catalyst solution to the reactor.

In a preferred embodiment of the present invention the process ligand and the second ligand are fed together to the process, preferably to a portion of the recycled catalyst solution at 50° C. or below, either continuously or periodically.

According to an advantageous aspect of the present invention, when adding the second ligand to the process and in particular to a mixture containing catalyst system, the coordinated and free ligand/Pd ratio can be increased to above 1/1 under carbonylation conditions. As a typical example, when a coordinated bis(9-phospha-bicyclononyl)ethane derivative is at least partially destroyed, for example by oxidation and phosphonium salt formation, the second ligand (e.g., triphenylphosphine or a bis(diphenyl-phosphino)alkane) is taking over the role of the process ligand by coordinating to Pd. In this way sub-stoichiometric ligand/Pd ratios are avoided and the catalyst is stabilized.

In a further aspect of the invention the catalyst containing the above-described process ligand can be regenerated from Pd-second ligand complexes by feeding the better coordinating fresh process ligand to the catalyst solution. In order to avoid the above-described degradation of the process ligand, the catalyst solution containing Pd-second ligand complexes is advantageously contacted with the fresh process ligand at 50° C. or below resulting in an efficient regeneration.

In another advantageous aspect of the present invention the degradation rate of the above-described process ligand can be established by determining the rate of the Pd-complex formation with the second ligand. Naturally, for the latter goal feeding of the process ligand and regeneration of the catalysts should be stopped temporarily. Typically, as Pd-second ligand complexes form after at least partial destruction of the coordinated process ligand, the rate of Pd-second ligand complex formation is related to the rate of the degradation of the process ligand. Anyone skilled in the art will be able to determine these rates by carrying out appropriate measurements for example by $^{31}P$ NMR spectroscopy.

Another advantage of adding such second phosphine ligand to the process of the present invention is that—without wishing to be bound to any theory—the second ligand, which has less coordination strength in Pd-complexes than the above-described process ligand, oxidizes faster than the process ligand. In other words, a second ligand can be used as a "sacrifice" ligand thereby protecting the oxidation of the coordinated process ligand. The oxidation of the coordinated process ligand might for example occur by residual oxygen contents in the reactants or by air in-leak. At some conditions residual water contents might also cause oxidation of coordinated ligand. As a result the Pd catalyst complex becomes sub-stoichiometric in ligand at some point of the continuous carbonylation process due to the absence of available free ligand. Sub-stoichiometric ligand/Pd ratios tend to give fouling and losses of the catalyst via Pd-black formation under carbonylation conditions. As stated above, the coordinated and free ligand to Pd ratio must be kept at 1 to 1 or above by adding or feeding fresh ligand to the system in a continuous process in order to avoid Pd-losses.

The conjugated diene preferably is a conjugated diene having from 4 to 20, or preferably from 4 to 8 carbon atoms per molecule. Examples of suitable conjugated dienes include 1,3-butadiene, 1,3-pentadiene, 1,3-hexadiene, 1,3-cyclohexadiene, 2,4-heptadiene, and 2-methyl-1,3-butadiene. Preferably, the conjugated diene is 1,3-butadiene.

Preferred hydroxyl group-containing compounds in the process of the present invention are alkanols with 1 to 20, more preferably with 1 to 6 carbon atoms per molecule and alkanediols with 2-20, more preferably 2 to 6 carbon atoms per molecule. The alkanols can be aliphatic, cydoaliphatic or aromatic. Suitable alkanols in the process of the present invention include methanol, ethanol, ethanediol, propanol, 1,3-propanediol, iso-propanol, butanol, iso-butanol, tert. butanol, pentanol, hexanol, cyclohexanol and phenol. Preferably methanol or ethanol is used as a hydroxyl group containing compound.

The use of these alkanols or alkanediols as a hydroxyl group containing compound in the carbonylation process of 1,3-butadiene enables the production of alkylpentenoates and alkyladipates of which the alkyl group contains 1 to 20, more preferably 1 to 6 carbon atoms.

The process according to the present invention is particularly suitable for the production of alkylpentenoates and dialkyladipates by carbonylating 1,3-butadiene in the presence of an appropriate hydroxyl group-containing compound. Methanol and ethanol are preferred hydroxyl group-containing compounds. The use of methanol as hydroxyl group-containing compound in the carbonylation of 1,3-butadiene, which is a preferred embodiment of the invention, enables the production of methyl pentenoates and/or dimethyladipate. Dimethyladipate is an intermediate compound in the preparation of adipic acid, an intermediate compound to prepare Nylon 6,6. Methylpentenoates are important intermediates in the production process of $\epsilon$-caprolactam. For the preparation of $\epsilon$-caprolactam, a mixture of methylpentenoates is hydroformylated to methyl formylvalerate, which after reductive amination and cyclisation forms $\epsilon$-caprolactam. $\epsilon$-Caprolactam is a starting material in the manufacture of Nylon 6 fibres or engineering plastics. Hydroformylation, reductive amination and cyclization can be performed in any manner known to a person skilled in the art. Suitable processes are described, e.g., in WOA-9733854, WO-A-9835938 and WO-A-9837063.

In the process of the present invention, liquid carbonylation product and/or surplus of a carbonylation reactant such as conjugated diene or hydroxyl group containing compound will serve as solvent during the reaction. It is also possible to perform the reaction in the presence of an extra inert solvent. Suitable extra inert solvents are for example aprotic compounds. Examples include saturated hydrocarbons, such as for example aromatic hydrocarbons, paraffins and isoalkanes; ketones, such as for example methylbutylketone; ethers, such as for example, anisole, 2,5,8-trioxanonane (diglyme), dioxane, tetrahydrofurane, diphenylether, diisopropylether and the dimethylether of diethyleneglycol; esters, such as for example methylacetate, dimethyladipate and butyrolactone; amides, such as for example dimethylacetamide and N-methylpyrrolidone; and sulfones, such as for example diisopropylsulfone, sulfolane, 2-methylsulfolane and 2-methyl-4-ethylsulfolane. More preferably, the carbonylation is carried out in a mixture of liquid carbonylation products and/or surplus of a carbonylation reactant such as butadiene and methanol in the absence of an extra inert solvent.

The carbonylation is suitably carried out at moderate reaction conditions. Hence temperatures in the range of 20 to 200° C. are recommended, preferred temperatures being in the range of 70 to 160° C.

Carbon monoxide pressures in the range of 0.1-6.5 MPa are preferred. In the process according to the present invention, the carbon monoxide can be used in its pure form or diluted with an inert gas such as nitrogen, carbon dioxide or noble gases such as argon. Small amounts of hydrogen can also be present. In general, the presence of more than 5% hydrogen is undesirable, since this can cause hydrogenation of the conjugated diene.

The molar ratio of hydroxyl group containing compound to conjugated dienes, in particular butadiene, can vary between wide limits and suitably lies in the range of 0.1:1 to 10:1, more suitably from 1:1 to 6:1. The molar ratio of conjugated diene, in particular butadiene, to palladium can vary between wide limits, suitably in the range from $1 \times 10^1$ to $2 \times 10^7$ moles of conjugated diene per mole of palladium, depending also on the concentration of palladium used. When a preferable palladium concentration is used as given below, the molar ratio of conjugated diene to palladium is kept usually between 10 and 3000, most preferably between 50 and 1000.

The concentration of the preferred carboxylic acid or a mixture of the preferred carboxylic acids, which are described above as anion source, can vary in a wide range between 0 and to above 90 wt % in the reaction mixture. Preferably, the concentration of the anion source is kept between 1 and 10 wt % in the reaction mixture. The molar ratio of above-described halide anions, if any, to palladium is kept preferentially in the range between 0.001 and 0.5.

The palladium concentration in the reaction mixture is preferably as high as possible because the production rate per unit of reactor volume will be higher. The upper limit will normally be determined by the solubility of palladium in the reaction mixture. The upper limit can be determined by anyone skilled in the art. Preferably, the amount of palladium is between 100 and 6000 ppm and more preferably between 600 and 2000 ppm.

As described above, it is preferable to keep the process ligand/palladium molar ratio at 1.0 or slightly above. Attempts to increase the process ligand to palladium ratio to above 1.1 by feeding more process ligand will lead to an undesirable increase in the consumption of the process ligand. When performing the process of the invention It will be preferred to monitor the concentration and degradation rate of the process ligand during the course of the carbonylation process. In the most preferred embodiment of the invention, the process ligand is fed into the system in the above-described manner exactly by the rate it is consumed.

When a second ligand is applied according to the present invention, the molar ratio of the second ligand to palladium may vary in the process in wide ranges between 0 to above 100. Preferably, when the second ligand is applied, its concentration and degradation rate is also monitored. Most preferably, when a second ligand is applied, the second ligand is fed to the process under the above-described manner exactly by the rate it is consumed and the molar ratio of second ligand to palladium is kept between 0.001 to 10.

The process ligand is preferably added in an organic solvent, in particular a solvent selected from the group, which is described above as possible solvent for the carbonylation. Preferably, the solvent for the process ligand is selected from the group consisting of an alkanol, a $C_6$-diester, or a mixture of two or more of these compounds. Most preferably, the process ligand is added in methanol or dimethyladipate. The above-described second ligand when applied is preferably added in a similar solvent.

Figure 1:
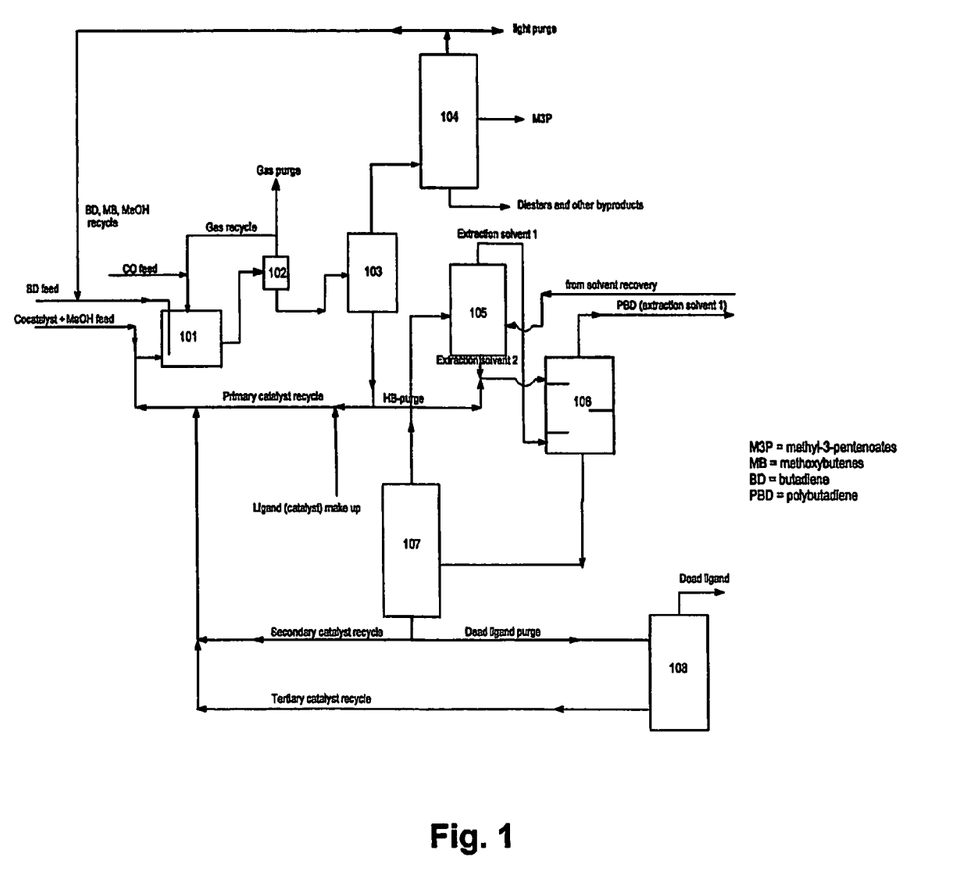
FIG. 1 is a schematic drawing of an embodiment of the process according to the present invention.

FIG. 1 is a schematic drawing of an embodiment of the process according to the present invention. FIG. 1 is an illustration of a continuous process for the carbonylation of 1,3- butadiene. It should be noted that generally partial purges can be applied in the various streams which are not shown in FIG. 1 for the sake of simplicity.

A reactor (101), or a series of reactors, is continuously fed with appropriate amounts of carbon monoxide, 1,3butadiene, methanol and a solution of a Pd-based catalyst at reaction conditions suitable for carbonylation, for example a pressure of 50 bar and a reaction temperature of 135° C. The Pd-based catalyst solution contains Pd complexes with one or two different organophosphorus ligands, appropriate amounts of the non-coordinated, free form of this ligand or of said ligands and a source of anions. A stream comprising unreacted 1,3-butadiene, methanol, carbon monoxide, Pd-based catalyst, diesters (e.g dimethyl adipate and possibly other $C_6$-diesters formed during the reaction), methylpentenoates, polymeric byproducts; and some other compounds such as methoxybutenes, methoxymethylvalerate; and acid components such as monomethyladipate, other mono esters of $C_6$-dibasic acids, pentenoic acids, adipic acid, pivalic acid etc. is withdrawn from the reactor (101), and led into a gas-liquid separator (102).

A stream of gas containing mainly carbon monoxide and butadiene is withdrawn from the top of the gas-liquid separator (102) and at least a portion thereof is recycled into the reactor. A stream of liquids containing dissolved Pd-based catalyst, possibly some 1,3-butadiene, methanol, diesters, methylpentenoates, polymeric byproducts and some other compounds such as methoxybutenes, methoxymethylvalerate; and acid components such as monomethyladipate, other mono esters of $C_6$-dibasic acids, pentenoic acids, adipic acid, pivalic acid etc. is withdrawn at the bottom of gas-liquid separator (102), and led into a flash vessel (103).

A stream of light components such as unconverted 1,3-butadiene, methanol, metoxybutenes, methylpentenoates, diesters, pentenoic acids and other components is withdrawn at the top of the flash vessel (103), and led into a distillation column (104) (or a series of distillation columns). A stream of unconverted 1,3-butadiene, methoxybutenes and methanol is withdrawn from the distillation column, and at least partially reduced into the reactor (101). Furthermore, methylpentenoates are separated in the distillation column (104) from diesters and other byproducts.

A stream containing Pd-based catalyst, diesters, methylpentenoates, polymeric byproducts and some other compounds such as methoxymethylvalerate; and acid components such as monomethyladipate, other mono esters of $C_6$-dibasic acids, pentenoic acids, adipic acid, pivalic acid etc. is withdrawn at the bottom of the flash vessel. From this stream a high boiler purge stream is withdrawn, and a main stream is recycled to the reactor (101).

The high-boiler purge stream is led into a multistage extraction unit (106). in the multistage extraction column polymeric byproducts are extracted from the high boiler stream by using two different and immiscible extraction solvents. Examples of suitable solvent couples for the extraction of polymeric by-products include acetonitrile with n-heptane and methanol with n-dodecane (or other paraffins). A stream, which is rich in polymeric by-product and poor in Pd-based catalyst, is removed from the top of the extractor (106). The extraction solvents are recovered from this stream by distillation and recycled to a solvent separation vessel (105).

A stream, which is rich Pd-based catalyst and poor in polymeric by-products is withdrawn at the bottom of extraction unit, and led to a distillation column (107) in order to at least partially recover the extraction solvents. A stream containing the extraction solvents and possibly a small amount of methylpentenoates, diesters and other products is withdrawn from the top of the distillation column (107), and led to a solvent separation vessel (105). Another stream containing Pd-based catalyst, diesters, methylpentenoates, methoxymethylvalerate; and acid components such as monomethyladipate, other monoesters of $C_6$-dibasic acids, pentenoic acids, adipic acid, pivalic acid etc., is withdrawn at the bottom of the distillation column (107). From this stream a smaller purge stream is withdrawn, and the rest (secondary catalyst recycle) is recycled to the primary catalyst recycle and to the reactor (101).

The purge stream is led to an adsorption unit (or a series of adsorption units) where the ligand degradation products are separated from the Pd-based catalysts. Suitable approaches for this goal include adsorption of the ligand degradation products or ion exchange of Pd-based catalyst containing the non-degraded ligands. A solution of the separated Pd-based catalyst containing non-degraded ligands is recycled to the secondary and primary catalyst recycles and to the reactor (101). The stream of the separated degraded ligands can be destroyed, for example by incineration. A stream of a solution of the organophosphorus ligand or of a mixture of two different organophosphorus ligands (ligand make-up stream) and eventually of a Pd source can be added to the primary catalyst recycle stream (FIG. 1), or to the secondary catalyst recycle stream, or to the tertiary catalyst recycle stream or to the united catalyst recycle stream.

In all of these cases, the ligand (catalyst) make-up stream will be contacted and mixed with the united catalyst recycle stream before entering the reactor (101). When a second ligand is used, it can be added periodically or continuously to the primary, secondary, tertiary or united catalyst recycle stream or directly into the reactor (101). A stream of a solution of an anion source such as a carboxylic add (add make-up stream) can for instance be added to the primary catalyst recycle, to the united catalyst recycle stream or directly into the reactor (101).

The invention is further illustrated by the following examples which should not be construed as limiting the present invention in any respect.

EXPERIMENTAL PART

Introduction

Figure 2:
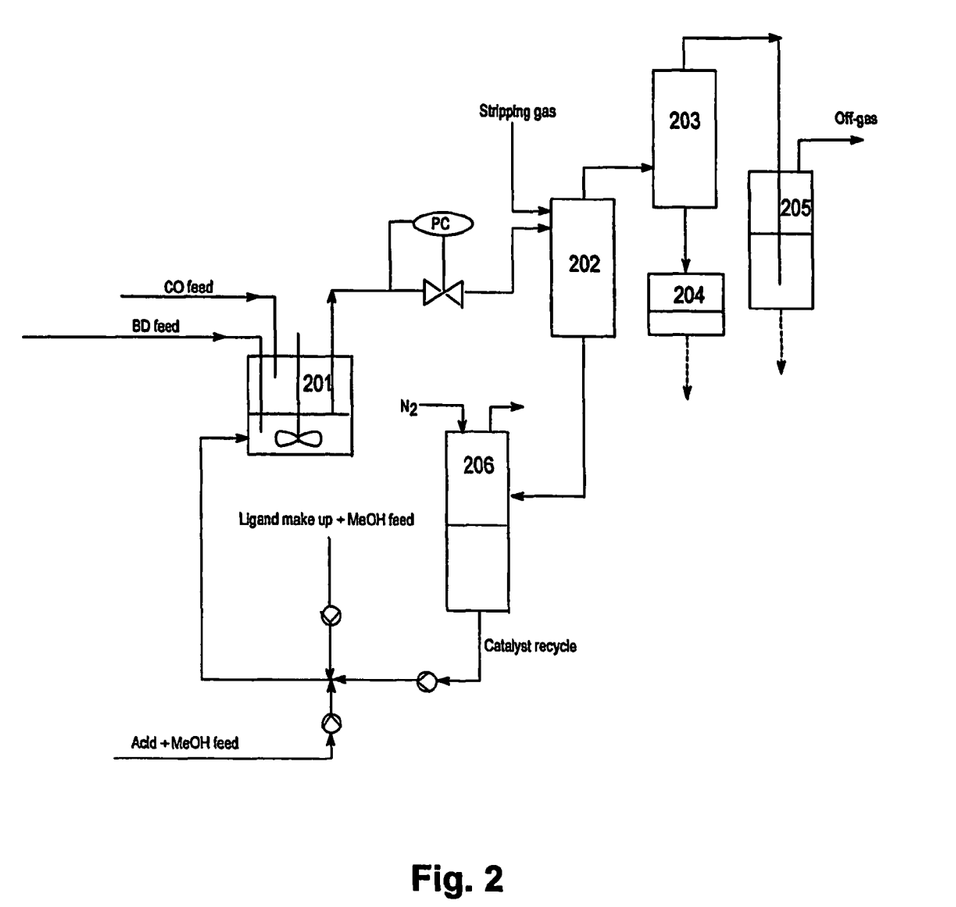
FIG. 2 is schematic drawing of a bench-scale unit that was used in conducting the experiments of Examples 1-4 and Comparative Experiments A-D below.

In order to carry out Examples 1-4 and Comparative Experiments A-D, a bench-scale unit was used as illustrated in FIG. 2. In this unit a stirred reactor (201) of 150 ml volume with 64 ml of liquid hold-up is continuously fed with appropriate amounts of carbon monoxide, 1,3-butadiene, methanol and a solution of a Pd-based catalyst at reaction conditions suitable for carbonylation. The Pd-based catalyst solution comprises Pd complexes with one or two different organophosphorus ligands, appropriate amounts of the non-coordinated, free form of this ligand or these ligands and a source of anions. A product stream is continuously withdrawn from the reactor and led into a stripper column (202).

Methylpentenoates, methoxybutenes, other light products and unreacted reactants are stripped off by a stream of pure nitrogen gas at the top of the stripper at suitable temperatures. The heavier components, including most of the methylpentenoates are condensed from the gas stream after stripping in a cooler (203). The condensed liquid components are collected in a product collector vessel (204) from the bottom of the cooler.

The vaporous products and unreacted reactants leaving the top of the cooler are washed out from the gas stream in a scrubber (205) or in series of scrubbers by using a suitable washing solvent. A stream containing a solution of the metal-based catalyst is continuously withdrawn at the bottom of the stripper (202) and led into the buffer vessel (206). The content of the buffer vessel is cooled to 50° C. or below. A stream containing a solution of the metal-based catalyst is taken from the buffer and mixed with a stream of a solution of the organophosphorus ligand or a mixture of two different organophosphorus ligands (ligand make-up stream) before feeding to the reactor.

Alternatively, a stream of a solution of the organophosphorus ligand or a mixture of two different organophosphorus ligands can also be added to the buffer vessel. A stream of a solution of an anion source such as a carboxylic acid (acid make-up stream) is added either to the recycled stream of the catalyst solution before feeding in the reactor or directly into the reactor. The performance of the bench-scale unit was monitored by determining the mass balances as follows. The contents of the collector vessel (204) and scrubber (205) were periodically removed, weighed back and analyzed by GC for composition and by ICP-MS for Pd- and P-concentrations. Parallel, the liquid volume was measured and samples were also taken from the liquid content in the buffer vessel (206). The samples from the buffer vessel were analyzed by GC for composition, ICP-MS for Pd-and P-concentrations, GPC for polybutadiene content and $^{31}$P NMR for catalyst composition. The conversion of butadiene was continuously measured from the off-gas by using an online GC with 5 wt % isobutane as an internal GC standard in the butadiene feed.

Example 1

A bench-scale unit as illustrated in FIG. 2 was operated for the continuous carbonylation of 1,3-butadiene into methylpentenoates using a homogeneous Pd-based catalyst system for 86 hours.

The catalyst solution was prepared under nitrogen by dissolving 370 mg of Pd acetate, 589 mg of 2,3-bis(9-phosphabicyclononyl)butane as process ligand and 1.96 g of pivalic acid with stirring in 98.9 g freshly distilled methylpentenoates containing 69.5% trans-methyl-3-pentenoate, 25.1% cis-methyl-3-pentenoate, 4.9% trans-methyl-2-pentenoate and small amounts of other methylpentenoate isomers, methoxybutenes, methanol, methylvalerate, 4-methoxy-methylvalerate and dimethyl esters of $C_6$-dibasic (adipic, methylglutaric, ethylsuccinic and 2-propylmalonic) acids. After a clear orange-brown solution was formed (15-30 minutes stirring), an amount of 21.6 µl hydrogen iodide (57 wt %) solution in water was added. The solution was stirred for another half an hour before transferring into the buffer-vessel.

At the start of the experiment, the reactor was brought under 50 bar pressure with carbon monoxide, then 5 ml of butadiene and 5 ml of methanol were pumped into the reactor at room temperature. Feeding of carbon monoxide, the catalyst solution, butadiene and methanol were started at rates of 6 l/h, 105 ml/h, 15 ml/h and 15 ml/h, respectively. The heating of the reactor was started and the temperature in the reactor was brought up to 135° C. in 2 hours by keeping the pressure at 50 bar and by maintaining the feeding values above. The stripper column was kept at 30° C. during this period using 20 l/h pure nitrogen for stripping.

When the reactor reached 135° C., the catalyst and butadiene feed was set to 29 ml/h and 7.67 ml/h, respectively. Parallel, the feeding of two different methanol solutions at room temperature to the high-pressure catalyst feed line was activated (FIG. 2). One of the methanol solutions contained 2,3-bis(9-phosphabicyclononyl)butane in 166 mg/l concentration. This solution was fed at 6 ml/h, which corresponds to 1 mg/h ligand feed. The other methanol solution contained pivalic acid in 35 g/l concentration. The latter solution was fed at 4 ml/h, which corresponds to a 0.14 g/h pivalic acid feed. The obtained mixed stream in the catalyst feed line, which was at room temperature, had 5 minutes residence time before entering the reactor. The temperature of the stripper column was first set to 90° C., and varied later between 90 and 110° C. as a way of controlling the liquid level in the buffer-vessel. For the same reason, the nitrogen flow to the stripper column was also varied between 20-50 l/h. These feed values were maintained until the end of the experiment, except that the solution of pivalic acid in methanol was replaced after 24 hours by a solution of monomethyladipate in methanol, which had 54.9 g/l concentration. The latter solution was fed also at a 4 ml/h rate, which corresponds to a 0.22 g/h monomethyladipate feed. The yield and selectivity to methylpentenoates was 263 g and 87%, respectively, after 86 hours. The mass balances calculated for the Pd and P contents showed that more than 99% of the Pd and P inventories are maintained in the recycled catalyst solution, distillate and scrubber fractions.

This Example indicates that the amount of ligand make-up feed used and the way it is implemented in this experiment is adequate for the stabilization of the catalyst.

Example 2

Example 1 was repeated, except that the experiment was carried out for 336 hours and the catalyst solution was made as follows: An amount of 240 mg of Pd acetate, 446 mg of 2,3-bis(9-phosphabicyclononyl)butane as process ligand, 2.08 g of triphenylphosphine as second ligand and 2.32 g of pivalic acid were dissolved in 52.6 g freshly distilled anisole under nitrogen with stirring. An amount of 30 mg of lithium pivalate in 5 ml of methanol as a tracer for ICP-MS analysis was also added to the solution. No hydrogen iodide was used in this experiment. Different from Example 1, carbon monoxide, the catalyst solution and butadiene were fed into the reactor at 10 l/h, 120 ml/h and 9 ml/h, respectively. Instead of two methanol solutions, an anisole and a methanol solution were fed to the high-pressure catalyst feed line at room temperature (FIG. 2). The anisole solution contained 2,3-bis(9-phosphabicyclononyl)butane in a concentration of 658 mg/l. This solution was fed at 3.6 ml/h, which corresponds to 2.37 mg/h ligand feed. The methanol solution contained pivalic acid in 6.85 g/l concentration. The latter solution was fed at 7.2 ml/h, which corresponds to a 0.049 g/h pivalic acid feed. Contrary to Example 1, the pivalic acid feed was maintained until the end of the experiment. Later on in the experiment, the butadiene and methanol acid feed were varied between 7-9 ml/h and 6-7.2 ml/h, respectively. After 160 hours, 1 g of triphenylphosphine in 5 ml anisole solution was added to the buffer vessel at room temperature. The yield and selectivity to methylpentenoates was 303 and 91%, respectively, after 336 hours. The mass balances calculated for the Pd and P contents showed that more than 99% of the Pd and P inventories are maintained in the recycled catalyst solution, distillate and scrubber fractions.

A $^{31}$P NMR spectrum recorded from a sample of the buffer vessel of the experiment at room temperature showed the presence of cationic π-methylallyl-Pd-2,3-bis (9-phosphabicyclononyl)butane complexes, dicarboxylate complexes of Pd-2,3-bis(9-phosphabicyclononyl) butane as well as other Pd complexes and various ligand degradation products including oxides and phosphonium salts of both ligands. No Pd complex with triphenylphosphine was detected. In contrast to 2,3-bis(9-phosphabicyclononyl) butane, which was also absent in the solution, triphenylphosphine was partly present in its uncoordinated form. About 70% and 40% of the triphenylphosphine and 2,3-bis(9-phosphabicyclononyl) butane content, respectively was present as oxide, which means that significantly more triphenylphosphine oxidized than 2,3-bis(9-phosphabicyclononyl)butane.

This Example shows that triphenylphosphine can be used as second ligand with this carbonylation system. Because of the excellent mass balance of Pd and of the fact that no Pd-triphenylphopsphine complexes were detected it can be concluded that the amount of ligand make-up feed used and the way it is implemented in this experiment are sufficient for the stabilization and regeneration of the catalyst.

Example 3

Example 1 was repeated, except that the experiment was carried out for 39 hours and the catalyst solution was made as follows: An amount of 218 mg of Pd acetate, 353 mg of 1,2-bis(9-phosphabicyclononyl)ethane as process ligand 862 mg 1,4-bis (diphenylphosphino)butane as second ligand and 1.90 g of pivalic acid were dissolved under nitrogen with stirring in 47.8 g freshly distilled anisole. No hydrogen iodide and lithium pivalate were used in this experiment; in contrast to Example 1, carbon monoxide, the catalyst solution, methanol and butadiene were fed at 10 l/h, 120 ml/h, 7.2 ml/h, 9 ml/h, respectively, into the reactor. Different from Example 1, no continuous feedings of a ligand make-up solution and an acid make-up solution were utilized in this experiment. After 13 hours, 2.2 g pivalic acid was added in one portion to the buffer vessel. The experiment was monitored from the start until the end by periodically taking $^{31}$P NMR samples under nitrogen from the buffer vessel. In the first hours of the experiment, $^{31}$P NMR spectra recorded at room temperature from the buffer samples showed the presence of cationic π-methylallyl-Pd-1,2-bis(9-phosphabicyclononyl)ethane complexes, dicarboxylate complexes of Pd-1,2-bis(9-phosphabicyclononyl)ethane as well as some ligand degradation products of this ligand including oxides and phosphonium salts. No free, uncoordinated 1,2-bis(9-phosphabicyclononyl) ethane was detected. In contrast to 1,2-bis(9-phosphabicyclononyl) ethane, bis(diphenylphophino)butane was present in its phosphonium salts, as free uncoordinated ligand and in a small amount of its oxide. No Pd complex with bis(diphenylphosphino)butane could be detected. After 12 hours of reaction time $^{31}$P NMR spectra showed similar composition to that above, except that the presence of small amounts of cationic π-methylallyl-Pd-1,4-bis(diphenylphosphino) butane complexes was clearly detected. In contrast to 1,2-bis(9-phosphabicyclononyl) ethane, 1,4-bis (diphenylphosphino)butane was still partly present as free uncoordinated ligand.

In the period from 12 to 34 hours the concentration of the cationic π-methylallyl-Pd-1,4-bis(diphenylphosphino)butane complexes gradually increased at the expense of cationic π-methylallyl-Pd-1,2-bis(9-phosphabicyclononyl)ethane complexes. At 34 hours of reaction time $^{31}$P NMR showed that 35% of the Pd-content was present in complexes with 1,4-bis(diphenylphophino)butane, mainly as cationic π-methylallyl-Pd-1,4-bis(diphenylphosphino)butane complexes. About 45% of the 1,4-bis(diphenylphosphino) butane content was present it its monoxide or dioxide derivatives with the rest being present in its phosphonium salts, Pd-complexes and uncoordinated form. In contrast to 1,4-bis(diphenylphosphino)butane, only about 10% of 1,2-bis(9-phosphabicyclononyl)-ethane was oxidized with the rest being phosphonium salts and Pd-complexes.

After 34 hours of reaction time a solution of 216 mg of 1,2-bis(9-phosphabicyclononyl) ethane in 13 ml anisole was fed into the buffer vessel at room temperature in 30 minutes (at a rate of 26 ml/h), which corresponded to a feed of 0.71 equiv. of fresh ligand per Pd. The contents of the buffer vessel (about 100 ml) were also at room temperature. A $^{31}$P NMR spectrum taken from the buffer vessel after the addition of fresh ligand showed that all the Pd complexes of 1,4-bis (diphenylphosphino)butane disappeared from the solution parallel with a sharp increase in the concentrations of uncoordinated 1,4-bis(diphenylphosphino)butane and cationic π-methylallyl-Pd-1,2-bis(9-phosphabicyclononyl)ethane complexes. Apparently, the catalyst was completely regenerated. A small amount of uncoordinated, free 1,2-bis(9-phosphabicyclononyl)ethane could also be detected in the sample.

Another sample was taken from the buffer vessel at 36.5 hours of reaction time. By this time, the contents of the buffer vessel passed the reactor (135° C., 50 bar) more than two times. The obtained $^{31}$P NMR spectrum showed essentially identical composition to that obtained right after the addition of fresh ligand, except that uncoordinated, free 1,2-bis(9-phosphabicyclononyl)ethane was no more detectable.

The yield and selectivity to methylpentenoates was 46 g and 91%, respectively, after 39 hours. The mass balances calculated for the Pd and P contents showed that more than 98% of the Pd and P inventories are maintained in the recycled catalyst solution, distillate and scrubber fractions.

This Example shows that 1,4-bis(diphenylphosphino)butane can be used as second ligand with this carbonylation system. It indicates also that the degradation of uncoordinated (excess) 1,2-bis(9-phosphabicyclononyl)ethane is slow at room temperature and fast under carbonylation conditions. The degradation of Pd-coordinated 1,2-bis(9-phosphabicyclononyl)ethane occurs under carbonylation conditions, for example by oxidation or through phosphonium salt formation, but at much slower rate than the uncoordinated ligand. For this reason feeding of the process ligand or a mixture of process ligand and second ligand is required at some time in the continuous carbonylation process in order to avoid precipitation of Pd-black. As the second ligand is taking over Pd from the process ligand only after the coordinated process ligand is degraded or partially degraded, the second ligand can also be used for establishing the rate of the degradation of Pd-coordinated process ligand, i.e. for establishing the amount of process ligand make-up feed. Because of the excellent mass balance of Pd and of the fact that no Pd 1,4-bis-(diphenylphosphino) butane complexes were detected after feeding the process ligand, it can be concluded that the amount of ligand make-up feed used and the way it is implemented in this experiment are sufficient for the stabilization and regeneration of the catalyst.

Comparative Experiment A

Example 1 was repeated, except that the experiment was carried out for 64 hours and the catalyst solution was made as follows: an amount of 630 mg of Pd acetate, 1.90 g of 2,3-bis (9-phosphabicyclononyl)butane as process ligand and 5.78 g of pivalic acid were dissolved under nitrogen with stirring in 141.1 g freshly distilled methylpentenoates containing 63.5% trans-methyl-3-pentenoate, 21.6% cis-methyl-3-pentenoate, 5.0% trans-methyl-2-pentenoate and small amounts of other methyl-pentenoate isomers, methoxybutenes, methanol, methylvalerate, 4-methoxy-methyl-valerate and dimethyl esters of $C_6$-dibasic (adipic, methylglutaric, ethylsuccinic and 2-propylmalonic) acids. No second ligand was used in this experiment An amount of 37 μl hydrogen iodide (57wt %) solution in water was added to the catalyst solution after dissolution of the components above. Different from Example 1, carbon monoxide, the catalyst solution and butadiene were fed into the reactor at 4 l/h, 10 ml/h and 6.99 ml/h, respectively. Contrary to Example 1, no feeding of a ligand make-up solution was utilized in this experiment. Instead of two methanol solutions, only one methanol solution and pure methanol were fed to the high-pressure catalyst feed line at room temperature. The methanol solution contained pivalic acid in 44.2 g/l concentration. The latter solution was fed at 4.8 ml/h, which corresponds to a 0.21 g/h pivalic acid feed. Pure methanol was fed at 7.68 ml/h to the high-pressure catalyst feed line at room temperature. These feed values including that of the solution of pivalic acid were maintained until the end of the experiment. The yield and selectivity to methylpentenoates was 172 g and 86%, respectively, after 64 hours. The mass balances calculated for the Pd contents showed that only 85.4% of the Pd inventory is maintained in the recycled catalyst solution, distillate and scrubber fractions.

This Comparative Experiment indicates that the catalyst is not effectively stabilized in a continuous run when no use is made of a ligand make-up feed. It also demonstrates that the use of an initial excess of the process ligand without ligand feed is not enough measure in a continuous process for the stabilization of the Pd-based catalyst.

Example 4

2 ml sample was taken for $^{31}$P NMR measurement from the buffer-vessel under nitrogen after the experiment described in Example 1 had been carried out. The contents of the sample included dimethyladipate as major component; other carbonylation products such other $C_6$-diesters, 4-methoxymethylvalerate methylpentenoates, partially carbonylated polybutadiene; and acid components such as monomethyladipate, other mono esters of $C_6$-dibasic acids, pentenoic acids, adipic acid, pivalic acid etc. The Pd and P concentration in the buffer vessel was measured by ICP-MS as 885 and 814 ppm, respectively. A $^{31}$P NMR spectrum recorded from the sample at room temperature showed the presence of cationic π-methylallyl-Pd-2,3-bis(9-phosphabicyclononyl)butane complexes, dicarboxylate complexes of Pd-2,3bis(9-phosphabicyclononyl)butane as well as other Pd complexes and various ligand degradation products including oxides and phosphonium salts. No free, uncoordinated ligand was detected. Next, 22 mg of 2,3-bis(9-phosphabicyclononyl) butane and 0.4 ml degassed methanol were added to the solution under nitrogen. A $^{31}$P NMR spectrum recorded afterwards at room temperature showed the presence of the free, uncoordinated ligand with an integrated ratio of 71.2% of the total P-content, which was in good agreement with the theoretical value. The solution was kept then at room temperature for 60 minutes. A $^{31}$P NMR spectrum recorded afterwards at room temperature showed no change in the composition.

This Example indicates that ligand degradation is negligible at room temperature.

Comparative Experiment B

The solution obtained in Example 4 was heated to 100° C. under nitrogen in a high pressure NMR tube. A $^{31}$P NMR spectrum recorded after 20 minutes heating at 100° C. showed the presence of the free, uncoordinated ligand only with an integrated ratio of 28.6% of the total P-content, which corresponds to a 59.8% degradation of the fresh ligand added in Example 4. The formed ligand degradation products included various phosphonium salts and three-valent P-components other than 2,3-bis(9-phosphabicyclo-nonyl) butane. After 60 minutes heating at 100° C., $^{31}$P NMR showed an 84.8% degradation of the fresh ligand added in Example 4.

This Example shows that when a ligand make-up is used of 2,3-bis(9-phosphabicyclononyl) butane, adding the fresh ligand to the recycled catalyst solution at 100° C. is not effective.

Comparative Experiment C

Another 2 ml portion was taken for from the buffer-vessel under nitrogen after the experiment described in Example 1 had been carried out. The solution had the same composition as described above in Example 4. Next, 32 mg of 2,3-bis(9-phosphabicyclononyl)butane and 0.5 ml degassed methanol were added to the solution under nitrogen in a high pressure NMR tube. Then 0.4 ml liquid butadiene was added and the tube was pressurized to 15 bar with CO. A $^{31}$P NMR spectrum recorded afterwards at room temperature showed the presence of the free, uncoordinated ligand with an integrated ratio of 78.2% of the total P-content, which was in good agreement with the theoretical value. After this, the solution was heated to 100° C. A $^{31}$P NMR spectrum recorded after 45 minutes heating at 100° C. showed the presence of the free, uncoordinated ligand only with an integrated ratio of 26.1% of the total P-content, which corresponds to a 66.7% degradation of the fresh ligand. After 65 minutes heating at 100° C., $^{31}$P NMR showed an 82.7% degradation of the fresh ligand.

This Example shows that, when a ligand make-up is used of 2,3-bis(9-phosphabicyclononyl)butane, adding the fresh ligand to the catalyst solution in the presence of butadiene, carbon monoxide and methanol at 100° C., i.e. lower than typical carbonylation temperatures, is not effective.

Comparative Experiment D

Example 4 was repeated except that an amount of 24 mg of 2,3-bis(9-phosphabicyclononyl)butane was used and the solution was heated to 50° C. A $^{31}$P NMR spectrum recorded after 15 minutes heating at 50° C. showed the presence of the free, uncoordinated ligand with an integrated ratio of 69.5% of the total P-content, which corresponds to a 4.9% degradation of the fresh ligand. After 90 minutes heating at 50° C., $^{31}$P NMR showed a 21.1% degradation of the fresh ligand.

This Example shows that degradation of the ligand make-up occurs, although relatively slowly, when adding the ligand to the recycled catalyst solution at 50° C.

The invention claimed is:

1. A process for the production of alkylpentenoate by carbonylation of 1,3-butadiene comprising reacting 1,3-butadiene with carbon monoxide and a hydroxyl group-containing compound in the presence of a palladium catalyst system in a reaction zone to produce a reaction mixture with a selectivity to alkylpentenoate reaction product of 87% and higher, said catalyst system comprising:
   (a) a source of palladium cations,
   (b) a phosphine process ligand which is at least one selected from the group consisting of 2,3-bis(9-phosphabicyclononyl)butane, 1,2-bis(9-phosphabicyclononyl)ethane, 1,2-bis (9-phosphabicyclononyl) propane, 1,2-bis (carboxymethyl)-1,2-bis(9-phosphabicyclononyl) ethane, 1,2-bis (hydroxymethylene)-1,2-bis(9-phosphabicyclononyl) ethane, 1,2-bis (methoxymethylene)-1,2-bis(9-phosphabicyclononyl)ethane, 1,2-bis(9-phosphabicyclononyl) cyclohexane, 1,2-bis(9- phosphabicyclononyl)benzene, 1,2- bis (9-phosphabicyclononyl)cyclopentane, 3,4-bis (9-phosphabicyclononyl)hexane, 2-bis (dicyclohexylphosphino)-3-(9-phosphabicyclononyl)butane, 1,2-dicyclohexyl-1,2-bis (9-phosphabicyclononyl)ethane and 1-cyclohexyl-1,2-bis(9-phosphabicyclononyl)ethane, and (c) a source of anions containing a carboxylic acid, wherein the process further comprises, feeding the process ligand (b) continuously or periodically into the process as ligand make-up at a temperature of 50° C. or lower, and feeding a second phosphine ligand different from the process ligand (b) continuously or periodically to the process as ligand make-up, wherein said second phosphine ligand contains at least one phosphorous atom which is connected to two aryl groups and is chosen such that a phosphonium salt of the second phosphine ligand is reversible under carbonylation conditions.

2. A process as claimed in claim 1, wherein each of the process ligand (b) as ligand make-up and the second phosphine ligand as ligand make-up is added to the reaction mixture containing at least a portion of the catalyst system.

3. A process as claimed in claim 2, wherein said process is performed as a continuous process.

4. A process as claimed in claim 1, wherein said process further comprises separating the alkylpentenoate reaction product from said reaction mixture to obtain a catalyst mixture containing at least a portion of said catalyst system and recycling at least a portion of said catalyst mixture to the reaction zone.

5. A process as claimed in claim 3, wherein said process further comprises separating high boiling compounds and/or dead ligand from said catalyst mixture and recycling the mixture containing catalyst obtained in the high boiler purge/catalyst separation zone and/or obtained in the dead ligand/catalyst separation zone to the reaction zone.

6. A process as claimed in claim 4, wherein each of the process ligand (b) as ligand make-up and the second phosphine ligand as ligand make-up is added to said catalyst mixture prior to feeding said catalyst mixture to the reaction zone.

7. A process as claimed in claim 5, wherein each of the process ligand (b) as ligand make-up and the second phosphine ligand as ligand make-up is added to the mixture containing catalyst prior to feeding said mixture to the reaction zone.

8. A process according to claim 5, wherein said mixture containing catalyst is united with the catalyst mixture prior to feeding said catalyst mixture to the reaction zone resulting in a united catalyst mixture, and wherein each of the process ligand (b) as ligand make-up and the second phosphine ligand as ligand make-up is added to the united catalyst mixture.

9. A process according to claim 1, further comprising monitoring the concentration and degradation rate of the process ligand during the course of the carbonylation process and thereby determine a consumption amount of the process ligand (b), and adding the second phosphine ligand in an amount sufficient to make-up the consumption amount of the process ligand (b).

10. A process as claimed in claim 1, wherein said second phosphine ligand has less coordination strength to palladium than the process phosphine ligand.

11. A process as claimed in claim 1, wherein said second phosphine ligand is a triaryl phosphine or a bis(diarylphosphino) alkane.

12. A process as claimed in claim 11, wherein said second phosphine ligand is selected from the group consisting of triphenyl phosphine, a substituted triphenylphosphine, a trinaphthylphosphine, a substituted trinaphthylphosphine or a bis (diphenylphosphino) alkane derivative having 2-8 carbons between the phosphorus atoms, straight or branched.

13. A process as claimed in claim 1, wherein the second phosphine ligand is fed to the process together with the process ligand as ligand make-up.

14. A process as claimed in claim 1, wherein the process ligand is added in an organic solvent for the process ligand, wherein the organic solvent is selected from the group consisting of an alkanol, a C6-diester, or a mixture thereof.

15. A process as claimed in claim 1, wherein the hydroxy-group containing compound is methanol or ethanol.

16. A process as claimed in claim 1, wherein the carboxylic acid is selected from the group consisting of pivalic acid, monomethyladipate, 3-pentenoic acid, acetic acid or a mixture of two or more of these compounds.

17. A process as claimed in claim 1, comprising adding the second phosphine ligand as make-up ligand to the process ligand prior to feeding of the process ligand to the reaction zone.

18. A process as claimed in claim 1, wherein the alkylpentenoate is methyl pentenoate.

* * * * *